(12) United States Patent
Beindorff et al.

(10) Patent No.: US 7,001,621 B2
(45) Date of Patent: Feb. 21, 2006

(54) BLENDS OF URSOLIC ACID/OLEANOLIC ACID

(75) Inventors: Christiaan Beindorff, Vlaardingen (NL); Frederick William Cain, Wormerveer (NL); John Hugh Pierce, Sharnbrook (GB); Ulrike Schmid, Wormerveer (NL); Erik Schweitzer, Wormerveer (NL); Jeroen Nicolaas M. van Straalen, Wormerveer (NL)

(73) Assignee: Loders Croklaan B.V.., Wormerveer (NL)

( * ) Notice: Subject to any disclaimer, the term of this patent is extended or adjusted under 35 U.S.C. 154(b) by 699 days.

(21) Appl. No.: 09/863,439

(22) Filed: May 24, 2001

(65) Prior Publication Data

US 2002/0037882 A1 Mar. 28, 2002

(30) Foreign Application Priority Data

Jun. 5, 2000 (EP) .................................. 00304753

(51) Int. Cl.
*A61K 35/78* (2006.01)
(52) U.S. Cl. ...................... 424/765; 424/725; 424/727; 424/764; 514/786; 426/655
(58) Field of Classification Search ................ 424/725, 424/765, 727, 764; 514/786; 426/655
See application file for complete search history.

(56) References Cited

U.S. PATENT DOCUMENTS

| 4,752,606 A | * | 6/1988 | Snyckers et al. |
| 5,948,460 A | | 9/1999 | Kang et al. |

FOREIGN PATENT DOCUMENTS

| DE | 1 152 221 | 8/1963 |
| EP | 0 555 484 B1 | 6/1995 |
| JP | 09020674 | 1/1997 |
| JP | 09040689 | 2/1997 |
| SU | 827 066 | 5/1981 |
| SU | 1738215 | 6/1992 |

OTHER PUBLICATIONS

Bishop et al, Phytochemistry, 16(1):67-68, 1977.
Crouteau et al, Phytochemistry, 8(11):2219-2222, 1969.
Menezes et al, An. Acd. Bras. Ci., 70(4):761-766, 1998.
Bock et al, Die Nahrung, VCH Verlagsgesellschaft, Weinheim, 10(5):409-412, 1996.

* cited by examiner

*Primary Examiner*—Susan D. Coe
(74) *Attorney, Agent, or Firm*—Morgan, Lewis & Bockius, LLP

(57) ABSTRACT

Blends comprising a glyceride and ursolic acid and oleanolic acid in weight ratios of 1:99 to 99:1 that contain less than 20 wt % of natural apolar components and/or low molecular weight components, normally present in natural extract for ursolic acid and oleanolic acid do not display the negative off taste of the natural extracts anymore.

19 Claims, No Drawings

BLENDS OF URSOLIC ACID/OLEANOLIC ACID

Ursolic acid and oleanolic acid are known compounds that are also known for their health effects. References wherein these effects are disclosed are, e.g. JP 09/040 689; JP 09/067 249; CN 1 085 748; JP 1 039 973; JP 03/287 531; JP 03/287 430; EP 774 255; JP 07/258 098; JP 07/048 260; JP 01/132 531; FR 2 535 203; and JP 1 207 262. Compositions comprising ursolic acid and oleanolic acid in weight ratios of 1:99 to 99:1 can be obtained by extracting natural sources like fruit skins or herbs, in particular by extracting skins of apples, pears, cranberries, cherries and prunes. The extracts so obtained contain ursolic acid and oleanolic acid in amounts of about 5–60% and in weight ratios mentioned above. However, these extracts have a major drawback, i.e. the extracts display a severe negative off flavour and as the components are intended to be used as health components in food products and the consumer does not appreciate a negative off flavour while consuming his food, it would be a main advantage when mixtures of these components could be obtained containing sufficient amounts of ursolic acid and oleanolic acid to make them useful for application in foods as health component and that do not display the negative off flavour of the products available so far.

We studied whether we could obtain such products. In this study, we found that the negative off flavour of the ursolic acid/oleanolic acid mixture is due to the presence of natural apolar and/or low molecular weight components in the natural extracts known so far. The apolar components being defined as that fraction of an extract from fruit skins that is eluted from a polar silica gel column, preferably with a Alltech Econosphere Silica HPLC column (150*4.6 mm, 5 µm) with an eluent, preferably being either a mixture of hexane/toluene (50:50) or a mixture of toluene/ethylacetate/formic acid (500/200/16), in 0–7 mm. Low molecular weight components are detected by GC with a apolar column, preferably a Chrompack SIMDIST (10 m*0.53 mm, 0.1 µm filmthickness) or a Quadrex DB-5 (10 m*0.53 mm, 0.1 µm filmthickness) and a temperature program, preferably starting with 120° C. (1 min); then 20° C./min until 325°, then 5° C./min until 350° C. (5 min) with retention times from 0.5–7 mm. The preferred used carrier gas is hydrogen with a pressure of 15 psi.

We found a method wherewith the amount of these apolar and/or low molecular weight components could be reduced considerably i.e. to below a level that would result in a negative off flavour impression. The result of this method is a mixture comprising ursolic acid and oleanolic acid in a weight ratio of 1:99 to 99:1, preferably 5:95 to 95:5, most preferably 15:85 to 15:85 wherein the mixture contains less than 20 wt %, preferably less than 10 wt %, most preferably 1 to 6 wt % of the natural apolar and/or low molecular weight components as present in natural extracts for ursolic acid and oleanolic acid. The apolar and/or low molecular weight components were found to be components belonging to the class of hydrocarbons, alcohols, fatty acids, triglycerides, ketones and carbohydrates.

Although the above mix could be used as such in food products, it is preferred to use it as a blend with other components, in particular, as a blend with glycerides, preferably triglycerides. Therefore, our invention concerns blends of a health component and a glyceride wherein the health component is the mixture disclosed above and which blend contains 1 to 99 wt %, preferably 5–80 wt % of one or more components selected from mono-, di-, and triglycerides as the glyceride. The glyceride part of this blend preferably displays a solid fat content measured by NMR-pulse on a non-stabilised fat at the temperature indicated of:

5 to 90 at 5° C.
2 to 80 at 20° C. and
less than 15, preferably less than 10 at 35° C.

The solid fat content is measured by the well known NMR-pulse technique on a fat that is not stabilised, this means that the measurement was performed on a fat that was subjected to the following treatment:

Melt at 80° C., keep it at 80° C. for 15 min, cool it to 0° C. and keep it at 0°for 30 min, heat it to measurement temperature and keep it thereon for 30 mm and measure the N-value at this temperature.

Preferred blends that are good applicable in food products are blends comprising components A, B and C, wherein:

A=the health composition according to the invention and as formulated in claims 1 or 2

B=a solid fat with an N20 of more than 20, preferably more than 45, most preferably more than 60 and C=a fat having at least 40 wt % of fatty acids with 18 C-atoms and having one to three double bonds, in particular fish oils, fish oil concentrates or glycerides from conjugated linoleic acid.

A being present in amounts of more than 0.1 wt %, preferably 0.1 to 20 wt %, most preferably 0.2 to 10 wt % B being present in amounts of 8 to 90 wt %, preferably 25 to 75 wt %, most preferably 40 to 70 wt % and C being present in amounts of 0 to 85 wt %, preferably 15 to 65 wt %, most preferably 20 to 50 wt %.

In these blends the fat component B is preferably selected from the group consisting of palm oil; palm oil fractions; coccoa butter equivalents; palm kernel oil; fractions of palm kernel oil; hardened vegetable oils such as hardened palm oil; hardened fractions of palm oil; hardened soybean oil; hardened sunflower oil; hardened rape seed oil; hardened fractions of soybean oil; hardened fractions of rapeseed oil; hardened fractions of sunflower oil; mixtures of one or more of these oils and interesterified mixtures thereof.

Fat component C in general will be a liquid oil and is preferably selected from the group consisting of sunflower oil; olive oil; soybean oil; rape seed oil; palm oil olein; cotton seed oil; olein fractions from vegetable oils; high oleic vegetable oils such as HOSF (=high oleic sunflower oil) or HORP (=high oleic rape seed oil); fish oils; fish oil concentrates and CLA-glycerides.

The blends comprising components A, B and C as disclosed above have excellent properties for application in food products containing a fat phase.

The blends can also contain other known micronutrients such as vitamines and minerals. It was however found that it was very beneficial if the blends also contain isoflavones and/or flavones in amounts corresponding with 0.005 to 5% of the total amount of ursolic acid and oleanolic acid. In this way compositions are obtained that combine all the health aspects from the ursolic acid and oleanolic acid with the known health aspects from isoflavones respectively flavones (in particular those concerning women's health, in particular for postmenopausal women).

The blends according to the invention can be used in food products to provide the health aspects to the food product without giving a negative taste. Therefore part of our invention are also food products with a fat phase comprising at least partly the blend according to the invention and as formulated in claims 1 to 9. The food products can be selected from the group consisting of spreads (fat contents of 10 to 90 wt %); dressings; mayonnaises; cheese; ice creams; ice cream coatings; confectionery coatings; fillings; sauces and culinairy product. Very beneficial food products are the food products with a continous fat phase representing about 10 to 90 wt % of the food product.

Food supplements, comprising an encapsulated amount of the blends according to the invention are also claimed. The encapsulating material is suitably selected from: sugars, carbohydrates, gums, hydrocolloids, proteins and in particular gelatin.

According to a last embodiment of our invention our invention also concerns the process for the making of our novel blends. Therefore part of our invention also is a process for making a blend with the composition according to claims 1 and 9 wherein:

skins of fruit, in particular skins from apples, cranberries, cherries, prunes or pears are extracted with an organic solvent, in particular selected from the group consisting of ketones, esters, alcohols and hydrocarbons an extract containing a mixture of ursolic acid and oleanolic acid is isolated the organic solvent is removed from the extract and a mixture comprising ursolic acid and oleanolic acid is isolated this mixture obtained is dissolved in water or an organic solvent or a mixture thereof, preferably acetone/water in a weight ratio of 50/50 to 95/5 while heating, after the mixture is dissolved the solution obtained is cooled to a temperature of maximum 25° C. and crystals formed are separated as product from the rest.

The product is blended with 1-99 wt % of a glyceride mix

Particulars of Our Extraction Are:

Prior to the extraction, the fruit skins or herbs are dried to humidity lower than 10 wt %, preferably between 2 and 6 wt %. The skins are then powdered with an electric stirrer. Extraction was performed by mixing the particles with an organic solvent using 1 to 1000 kg of solvent per 1 kg of starting material, preferably 10 to 100 kg of solvent per 1 kg of starting material. The organic solvents are selected from the following groups: alkanes, ketones, esters, aldehydes, hydrocarbons, alcohols. Extraction was performed at temperatures between 0° C. and boiling temperature ($T_b$) of the organic solvent, preferably at temperatures between $T_{b-10}$° C. and $T_b$. The residence time for extraction is not less than 5 minutes, preferably between 15 and 60 minutes. After extraction, the remaining particles were filtered and the solvent was evaporated partly or completely. The remaining extract is washed by dissolving it in organic solvents or water or a mixture of these, at temperatures between 0° C. and the boiling temperature of the solvent, preferably at temperatures above 20° C. Washing is performed by contacting the extract and washing solvent for at least 15 minutes, preferably between 30 and 60 minutes. The extract is recovered by crystallisation in organic solvents or water or a mixture of these by cooling to temperatures below 25° C., preferably at 0° C., followed by filtration of the extract.

The blends can be made by a process wherein the mixture obtained above is mixed in appropriate amounts with a glyceride selected from the glycerides from claims 6 and 7 in amounts appropriate to give the correct amounts according to claim 5, whereupon the total blend is homogenised.

EXAMPLES

1. Lab Scale Extraction 400 g of ground apple skin was mixed with 2 l acetone. The extraction was performed at 58° C. for 3 h while stirring. After extraction the solvent was removed and the product dissolved in a mixture of water/acetone (10:90) by heating up to 60° C. Crystallization was performed at room temperature. After 15 min white crystals were formed which were separated by filtration (20° C.). The second crystallization was at 4° C. over night. The crystals were separated by filtration and dried under nitrogen. The content of ursolic acid and oleanolic acid was determined with GC by using cholesterol as an internal standard (example 3).

2. Large Scale Extraction

Extraction was performed in a 180 liter (solvent) crystalliser with a gate-stirrer with hot acetone at 45–50° C. for about 30 min at ambient pressure. 10 kg ground apple peel/pomace was slurried in 100 l acetone at 35° C. 10 min was allowed for heating to 45–50° C. After this preheating period, the temperature was kept constant between 45–50° C. for about 30 min. After extraction the slurry was led to the A4-filter (pore-size 40 µm) for filtration of the pomace waste. Before feeding the slurry to the filter, the filter was preheated with acetone at 50° C. Filtration was performed by putting up to 1 bar overpressure on the slurry. Filtration of the slurry was performed quickly to prevent crystal formation in the filter cake. The extract of the filtration was sampled to determine the yield and selectivity of the extraction. The evaporation was partly performed in the LUWA evaporator vessel at reduced pressure (50 mbar). Before the product was crystallised from the solvent, the extract product was filtered over a candle filter (10 µm) to remove the last remaining pomace particles. The remaining solvent (20 l) was evaporated in a separate evaporator/boiler. The dried solid extract was washed with demi-water to remove the water-soluble substances. The extract was washed with demi-water for three times, filtrated and dried overnight in an autoclave at 5–10 mbar pressure. The filtrate was washed with 250 ml demiwater, stirring for 0.5 h at 50° C. The mixture was cooled to 0° C. for crystallisation of the product. The product was filtrated over a black ribbon paper filter (10 µm) in a Buchner funnel. The product was resuspended in 250 ml of hexane and stirred for 0.5 h at 60° C. The mixture was cooled to 0° C. for crystallization of the product. The product was filtrated over a black ribbon paper filter (10 µm) in a Büchner funnel and dried as described before.

3. HPLC Analysis

The HPLC analysis to determine the apolar components was performed with the following equipment and conditions:

Apparatus and Equipment

Analytical balance; Alltech Econoshpere Silica HPLC column (150*4.6 mm, 5 µm)

Ternair HPLC pump; HPLC autosampler

Alltech 500 ELSD detector (low gain) drift-tube: 75° C.; Nebulizer: 1.75 L/min

HPLC Analysis

The gradient that is used for this analysis is described in the appendix. This gradient was run without injecting a sample to flush the column before injecting samples. 5 µL of the sample solution was injected into the HPLC system.

Gradients Used for Silica Straight Phase HPLC

Solvents: A: hexane/toluene (50/50)

B: toluene/ethylacetate/formic acid (500/200/16)

TABLE 1

| Determination of diglycerides | | | |
|---|---|---|---|
| time (min) | flow (mL/min) | A | B |
| initial | 0.9 | 95 | 5 |
| 2 | 0.9 | 95 | 5 |
| 3 | 0.9 | 95 | 5 |
| 5 | 0.9 | 90 | 10 |
| 7 | 0.9 | 75 | 25 |
| 8 | 0.9 | 50 | 50 |
| 15 | 0.9 | 10 | 90 |
| 23 | 0.9 | 10 | 90 |
| 31 | 0.9 | 95 | 5 |
| 35 | 0.0 | 95 | 5 |

4. GC Analysis

GC analysis to determine the ursolic acid and the low molecular weight components content was performed with the following equipment and conditions:

Injection volume: 0.4 μL (cold-on-column)

Column: Chrompack SIMDIST (10 m*0.53 mm, 0.1 μm filmthickness) or: Quadrex DB-5 (10 m*0.53 mm, 0.1 μm filmthickness)

Ovenprogram: 1: 120° C.–1 min–20° C./min, 2: 325° C.–0 min–5.0° C./min, 3: 350° C.–5 min Detection: FID (360° C.)

Carriergas: Hydrogen (column pressure: 15 psi)

Internal standard: Cholesterol

5. Taste Panel with Different Extracts

Seven panellists tasted the different extracts. Objective: Comparison of the taste of the crude extract with the purified extract in a white filling. Reference was the pure white filling.

| | Intensity score | | | | | |
|---|---|---|---|---|---|---|
| | 0 | 1 | 2 | 3 | 4 | 5 |
| White Filling | 7 s | | | | | |
| WF + 2% AE 1 | | | 2 s | 1 s | 1 s | 3 s |
| WF + 2% AE 2 | 1 s | 1 s | | 2 s | 3 s | |
| WF + 2% PAE 1 | 4 s | 3 s | | | | |
| WF + 2% PAE 2 | 3 s | 3 s | 1 s | | | |

0 = No taste at all; 1 = A trace of taste; 2 = Faint taste; 3 = A clear taste; 4 = A strong taste; 5 = A very strong taste; WF = White filling; AE = Apple extract; PAE = Pure apple extract; s = subjects 0=No taste at all; 1=A trace of taste; 2=Faint taste; 3=A clear taste; 4=A strong taste; 5=A very strong taste; WF=White filling; AE=Apple extract; PAE=Pure apple extract; s=subjects The majority of the panellists have tasted a clear negative taste for the crude extract. The purified extracts however, were assessed as tasteless or only had a trace of a taste.

6. Ursolic Acid Extract in an Ice Cream Coating Experimental

The recipe for the ice cream coatings was the following:

475 g dark Callebaut 811

25 g Fat

Two different fats were used:

| A | 25 g Coberine (reference) |
|---|---|
| B | 10 g ursolic acid extract/15 g Coberine |
| Coberine: | Cacao butter equivalent |

The following characteristics were determined by coating small magnum ice creams.

Dripping temperature (° C.)

Dripping time (s)

Drying time (s)

Coating weight as % of total weight

Flexibility

Results

TABLE 1

| Summary of results | | |
|---|---|---|
| Characteristic | Sample A | Sample B |
| Dipping temperature (° C.) | 40 | 40 |
| Dripping time (s) | 18 | 12 |
| Drying time (s) | 74 | 62 |
| Coating weight (%) | 38.5 | 46.7 |
| Flexibility[1] | –/+ | ++ |

[1]The flexibility was tested by hitting the ice cream on the table.
Flexibility index:
++ = does not break
+ = difficult to break
– = breaks
– – = breaks easily

CONCLUSION

Coating B were found to have a shorter dripping time than coating A. Although the coating weight is higher (and thus coating is thicker) for coating B, the drying time is shorter than for coating A. The coating with the ursolic acid extract showed the least contraction after drying.

7. Ursolic Acid Extract in a Filling

A filling was prepared according to the following recipe:

35% fat blend, 10% cacao powder, 7% skimmed milk powder, 48% sugar, 0.5% lecithin.

All the components of the recipe were mixed in a porcelain bowl at a temperature of 55° C. The particles of the mixture were minimised by the use of a mortar. The mixture was cooled to 29° C. before depositing in aluminium cups.

The blends to be evaluated were:

| 1. 40/10/50 | Equator 75/POfiv65/SF (reference) |
|---|---|
| 2. 40/10/40/10 | Equator 75/POfiv65/SF/apple extract |
| 3. 40/10/40/10 | Equator 75/POfiv65/SF/PO 60 |
| Equator 75: | Cacao butter stearin |
| POfiv65: | Oleïn fraction of palm oil with iodine value of 65 |
| PO 60: | Hardened palm oil with melting point of 60° C. |
| SF: | Sunflower oil |

The hardness of the three different blends were measurement with the Stevens Texture Analyser (STA) after 24 hours at 20° C., cone 60°, penetration 2 mm:

| Blend | 1 | 2 | 3 |
|---|---|---|---|
| Hardness | 42 | 718 | 501 |

Conclusion

The blend with ursolic acid extract were found to have better hardness then the reference and the filling with hardened palm oil.

8. Ursolic Acid in Chocolate

| | |
|---|---|
| Sample A | 475 g dark Callebaut + 25 g Coberine |
| Sample B | 475 g Callebaut + 10 g ursolic acid extract + 15 g Coberine |
| Sample C | 475 g dark Callebaut + 10 g PO 60 + 15 g Coberine |

The mixtures were tempered manually at 29° C. on a stone table at room temperature. Part of the chocolate was over tempered and then mixed with the non tempered chocolate to achieve a tempered chocolate mixture.

Heat Resistance

Samples (solid chocolate bonbon) are stored during 17 hours at 40° C.

| | | |
|---|---|---|
| Dimension at 20° C.: | All samples | 3.3 × 2.5 cm Height 1.9 cm |
| Dimension at 40° C.: | Sample A | 6.0 × 5.5 cm Height 0.4–0.6 cm |
| | Sample B | 3.4 × 2.6 cm Height 1.6–1.8 cm |
| | Sample C | 5.0 × 4.7 cm Height 0.5–0.7 cm |

Hardness

The settings on the Stevens Texture Analyzer were:
Distance: 2 mm
Speed: 0.5 mm/sec.

| Characteristic | Sample A | Sample B | Sample C |
|---|---|---|---|
| Hardness | 189 | 234 | 188 |

CONCLUSION

The highest heat resistance and hardness was observed with the ursolic acid extract containing sample.

The invention claimed is:

1. A blend of a health component and a glyceride, wherein the health component is a mixture comprising ursolic acid and oleanolic acid in a weight ratio of 1:99 to 99:1, wherein the mixture is isolated from fruit skins and contains less than 20 wt % of the natural apolar and/or low molecular weight components present in natural extracts for ursolic acid and oleanolic acid which provide an off taste to said natural extract, and wherein the blend contains 5–80 wt % of one or more components selected from mono-, di- and triglycerides as the glyceride and the glyceride part of the blend displays a solid fat content measured by NMR-pulse on a non-stabilised fat at the temperature indicated of:

5 to 90 at 5° C.
2 to 80 at 20° C. and
less than 15 at 35° C.

2. A blend according to claim 1 wherein the natural apolar and/or low molecular weight components that provide an off taste to the natural extract belong to the class of hydrocarbons, alcohols, fatty acids, triglycerides, ketones and carbohydrates.

3. A blended composition comprising, as component A, a blend according to claim 1 wherein a solid fat with an N20 of more than 20 as component B and, optionally, as component C, a fat having at least 40 wt % of fatty acids with 18 C-atoms and having one to three double bonds, component A being present in an amount of more than 0.1 wt %, component B being present in an amount of 8 to 90 wt % and component C being present in an amount of 0 to 85 wt %.

4. A blend according to claim 3 wherein fat B is selected from the group consisting of palm oil; palm oil fractions; cocoa butter equivalents; palm kernel oil; fractions of palm kernel oil; hardened vegetable oils such as hardened palm oil; hardened fractions of palm oil; hardened soybean oil; hardened sunflower oil; hardened rapeseed oil; hardened fractions of soybean oil; hardened fractions of rapeseed oil; hardened fractions of sunflower oil; mixtures of one or more of these oils and interesterified mixtures thereof.

5. A blend according to claim 3 wherein fat C is selected from the group consisting of sunflower oil; olive oil; soybean oil; rapeseed oil; palm oil olein; cottonseed oil; olein fractions from vegetable oils; high oleic oil; olein fractions from vegetable oils; high oleic vegetable oils such as HOSF or HORP, fish oils; fish oil concentrates and CLA-glycerides.

6. A blend according to claim 3 wherein component A also contains isoflavones and/or flavones in amounts corresponding with 0.005 to 5 % of the total amount of ursolic acid and oleanolic acid.

7. A blend according to claim 3 wherein component A is a component isolated from fruit skins selected from the group consisting of skins from apples, pears, cranberries, cherries and prunes.

8. A food product with a fat phase comprising the blend according to claim 1.

9. A food product according to claim 8 wherein the food product is selected from the group consisting of spreads having fat contents of 10 to 90 wt %; dressings; mayonnaises; cheese; ice creams; ice cream coatings; confectionery coatings; fillings; sauces and culinary products.

10. A food product according to claim 8 or 9 wherein the food product comprises 10 to 90 wt % of a continuous fat phase.

11. A food supplement comprising the blend according to claim 1 in encapsulated form.

12. A food supplement according to claim 11, wherein the encapsulating material is selected from: sugars, carbohydrates, gums, hydrocolloids and gelatin.

13. A blend according to claim 1 wherein the weight ratio of ursolic acid to oleanolic acid is 5:95 to 95:5 and the mixture contains less than 10 wt % of the natural apolar and/or low molecular weight components.

14. A blend according to claim 1 wherein the weight ratio of ursolic acid to oleanolic acid is 15:85 to 85:15 and the mixture contains 1 to 6 wt % of the natural apolar and/or low molecular weight components.

15. A blend according to claim 1 wherein the glyceride part displays a solid fat content measured by NMR-pulse on a non-stabilised fat of less than 10 at 35° C.

16. A blended composition according to claim 3 wherein component B is a solid fat with an N20 of more than 45.

17. A blended composition according to claim 16 wherein component B is a solid fat with an N20 of more than 60.

18. A blended composition according to claim 17 wherein component A is present in an amount of 0.1 to 20 wt %, component B is present in an amount of 25 to 75 wt % and component C is present in an amount of 15 to 65 wt %.

19. A blended composition according to claim 17 wherein component A is present in an amount of 0.2 to 10 wt %, component B is present in an amount of 40 to 70 wt % and component C is present in an amount of 20 to 50 wt %.

* * * * *